United States Patent
Møller

(10) Patent No.: US 6,663,602 B2
(45) Date of Patent: Dec. 16, 2003

(54) INJECTION DEVICE

(75) Inventor: Claus Schmidt Møller, Fredensborg (DK)

(73) Assignee: Novo Nordisk A/S, Bagsvaerd (DK)

( * ) Notice: Subject to any disclaimer, the term of this patent is extended or adjusted under 35 U.S.C. 154(b) by 3 days.

(21) Appl. No.: 09/882,536

(22) Filed: Jun. 14, 2001

(65) Prior Publication Data

US 2002/0052578 A1 May 2, 2002

Related U.S. Application Data

(60) Provisional application No. 60/275,790, filed on Mar. 14, 2001, and provisional application No. 60/214,470, filed on Jun. 27, 2000.

(30) Foreign Application Priority Data

Jun. 16, 2000 (DK) .......................................... 2000 00932
Mar. 7, 2001 (DK) .......................................... 2001 00372

(51) Int. Cl.$^7$ ................................................ A61M 5/00
(52) U.S. Cl. ...................... 604/211; 604/208; 604/207; 604/224; 222/390
(58) Field of Search ...................... 604/207–211, 232, 604/218, 234, 131–136, 139, 187, 181; 222/46–48, 16, 18, 282, 283, 309, 310, 325, 326, 336, 386, 390

(56) References Cited

U.S. PATENT DOCUMENTS

| | | | |
|---|---|---|---|
| 4,470,317 A | | 9/1984 | Sabloewski et al. |
| 4,498,904 A | * | 2/1985 | Turner et al. ................ 422/928 |
| 4,585,439 A | | 4/1986 | Michel |
| 4,883,472 A | | 11/1989 | Michel |
| 4,973,318 A | * | 11/1990 | Holm et al. ................ 604/208 |
| 5,112,317 A | | 5/1992 | Michel |
| 5,304,152 A | * | 4/1994 | Sams ........................ 604/207 |
| 5,626,566 A | * | 5/1997 | Petersen et al. ............ 222/309 |
| 5,743,889 A | | 4/1998 | Sams |
| 6,003,736 A | | 12/1999 | Ljunggren |
| 6,004,297 A | * | 12/1999 | Steenfeldt-Jensen et al. ................ 604/207 |
| 6,074,372 A | | 6/2000 | Hansen |
| 6,086,567 A | * | 7/2000 | Kirchhofer et al. ......... 604/211 |
| 6,096,010 A | * | 8/2000 | Walters et al. ............. 604/207 |
| 6,221,053 B1 | * | 4/2001 | Walters et al. ............. 19/80 R |
| 6,383,167 B2 | * | 5/2002 | Kirchhofer et al. ......... 604/232 |

FOREIGN PATENT DOCUMENTS

| | | |
|---|---|---|
| DE | WO 36 09 555 | 9/1987 |
| WO | WO 96/26754 | 9/1996 |
| WO | WO 98/57688 | 12/1998 |
| WO | WO 99/38554 | 8/1999 |

* cited by examiner

Primary Examiner—Brian L. Casler
Assistant Examiner—Cris Rodriguez
(74) Attorney, Agent, or Firm—Reza Green, Esq.; Richard W. Bosk, Esq.; Marc A. Began, Esq.

(57) ABSTRACT

An injection device for injection of set does of medicine from a cartridge has a nut that is screwed up along a threaded piston rod during a dose setting operation. The nut is screwed along the piston rod by rotating a dose setting drum. An injection button is coupled to the piston rod with a gear wheel transmission. Axial movement of the injection button causes a corresponding axial movement of the piston rod until the nut engages an abutment in the housing.

16 Claims, 4 Drawing Sheets

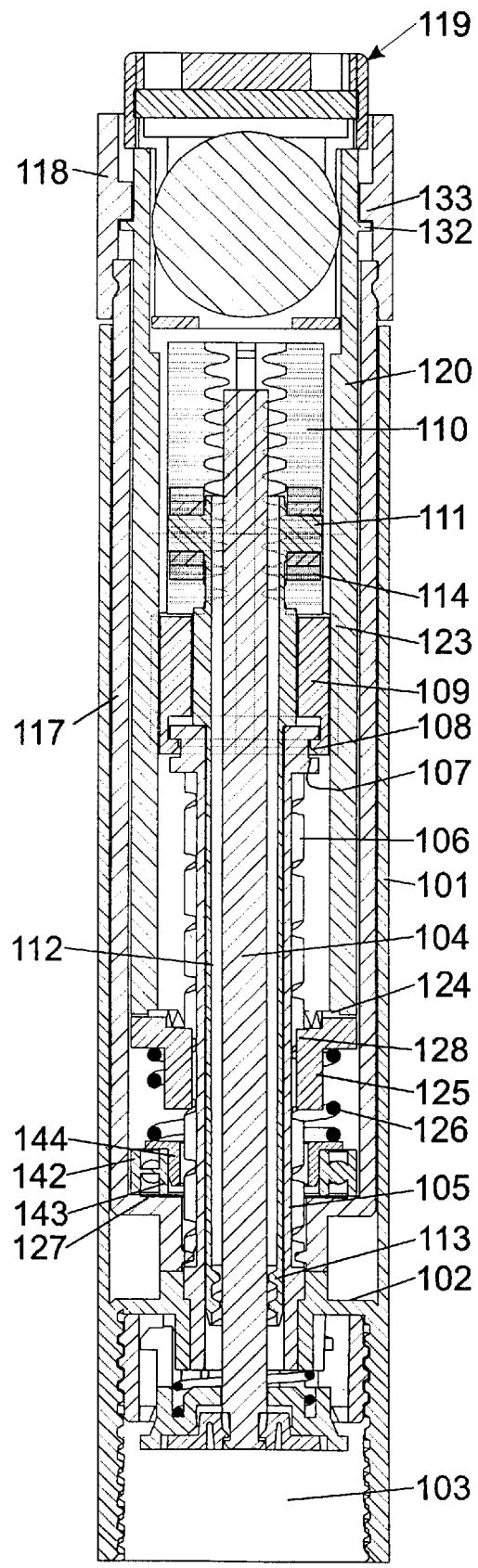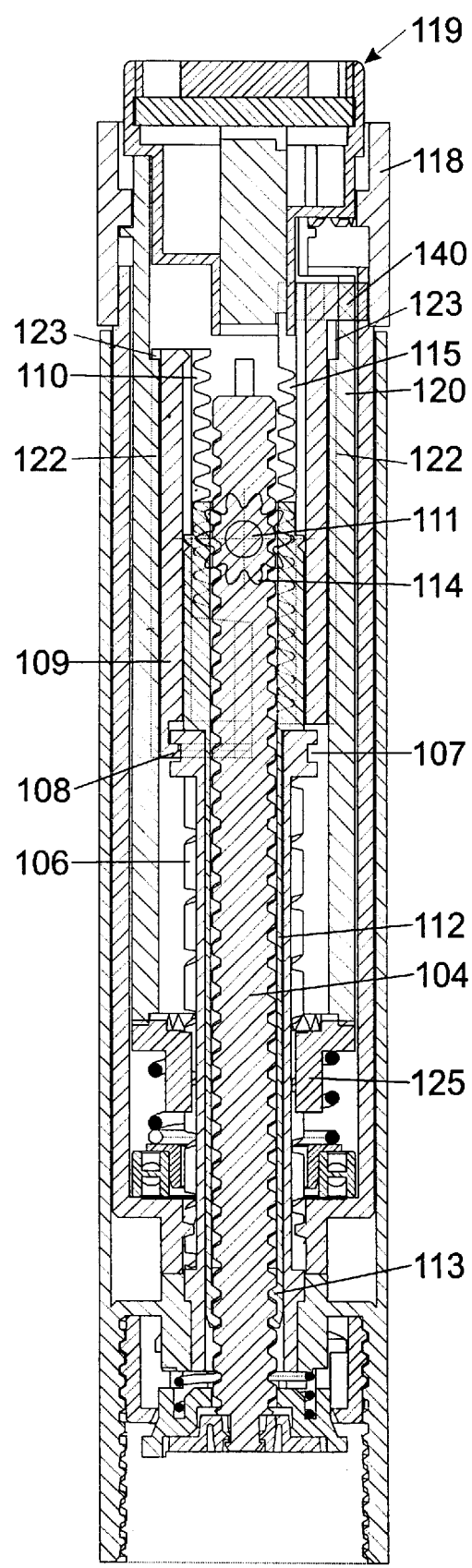

INJECTION DEVICE

CROSS REFERENCE OF RELATED APPLICATIONS

Figure 1:
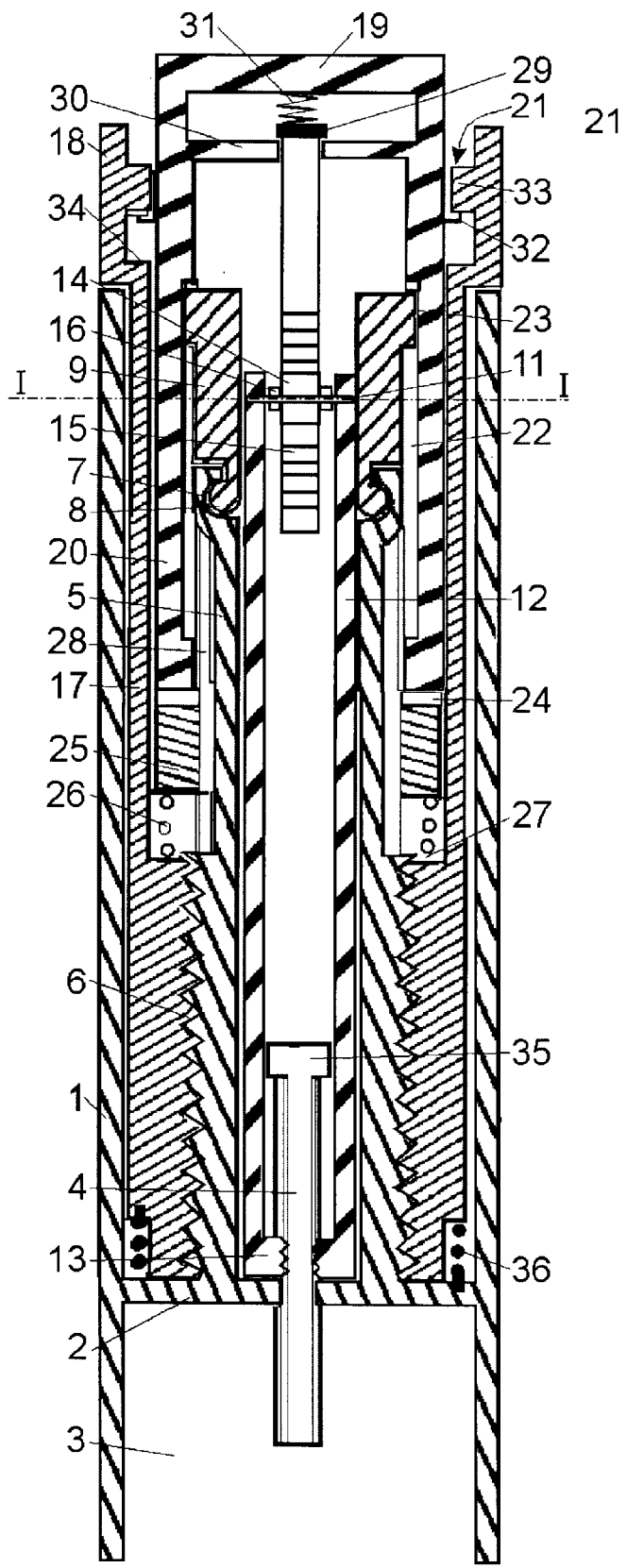

This application claims benefit of priority under 35 USC 119 of U.S. Provisional Applications Ser. Nos. 60/214,470, filed Jun. 27, 2000 and 60/275,790, filed Mar. 14, 2001, the contents of both are hereby incorporated by reference in their entirety. This application also claims benefit of priority under 35 USC 119 of Danish applications PA 2000 00932, filed Jun. 16, 2000 and PA 2001 00372, filed Mar. 7, 2001.

The invention relates to syringes by which a dose can be set by rotating a dose setting member and by which an injection button elevates from an end of the syringe a distance proportional to the set dose and wherein the set dose can be injected by pressing home the injection button to its not elevated position.

An almost classic pen of this type is described in EP 327 910.

By setting a dose on this pen a tubular member forming an injection button is screwed up along a threaded piston rod a distance corresponding to the distance said piston rod must be moved to inject the set dose. The tubular member simply forms a nut which is during the dose setting screwed away form a stop and which is during the injection pressed back to abutment with said stop and the force exerted on the button is directly transmitted to the a piston closing one end of an ampoule in the syringe which ampoule contains the medicament to be injected. When the piston is pressed into the ampoule the medicament is pressed out through a needle mounted through a closure at the other end of the ampoule.

By time it has been wanted to store larger amount in the ampoules, typically 3 ml instead of 1.5 ml. As it has not been appropriate to make the syringe longer the ampoule is instead given a larger diameter, i.e. the area of the piston facing the medicament in the ampoule has been doubled and consequently the force which has to be exerted on the piston to provide the same pressure as previously inside the ampoule has been doubled. Further the distance the piston has to be moved to inject one unit of the medicament has been halved.

This development is not quite favourable, as especially users having reduced finger strength have their difficulties in pressing the injection button, a problem that is further increased when still thinner needles are used to reduce the pain by injection. Also with quite small movements of the button it is difficult to feel whether the button is moved at all and by injection of one unit from a 3 ml ampoule the piston and consequently the injection button has to be moved only about 0.1 mm.

Consequently a wish for a gearing between the injection button and the piston has occurred so that the button has a larger stroke than has the piston. By such a gearing the movement of the injection button is made larger and the force, which has to be exerted on the injection button, is correspondingly reduced.

In EP 608 343 a gearing is obtained by the fact that a dose setting element is screwed up along a spindle having a thread with a high pitch. When said dose setting element is pressed back in its axial direction the thread will induce a rotation of said dose setting element, which rotation is via a coupling transmitted to a driver nut with a fine pitch which driver nut will force a threaded not rotatable piston rod forward.

A similar gearing is provided in WO 99/38554 wherein the thread with the high pitch is cut in the outer surface of a dose setting drum and is engaged by a mating thread on the inner side of the cylindrical housing. However, by this kind of gearing relative large surfaces are sliding over each other so that most of the transformed force is lost due to friction between the sliding surfaces. Therefore a traditional gearing using mutual engaging gear wheels and racks is preferred.

From WO 96/26754 is known an injection device wherein two integrated gear wheels engages a rack fixed in the housing and a rack inside a plunger, respectively. When the plunger is moved axially in the housing the rack inside this plunger can drive the first gear wheel to make the other integral gear wheel move along the fixed rack in the housing. Thereby the gear wheel is moved in the direction of the plunger movement but a shorter distance than is this plunger and this axial movement of the integrated gear wheels is via a housing encompassing said gear wheels transmitted to a piston rod which presses the piston of an ampoule further into this ampoule. However, the rack inside the plunger is one of a number axial racks provided inside said plunger. These racks alternates with untoothed recesses, which allow axial movement of the plunger without the first gear wheel being in engagement with a rack in this plunger. This arrangement is provided to allow the plunger to be moved in a direction out of the housing when a dose is set. When the plunger is rotated to set a dose it is moved outward a distance corresponding to one unit during the part of the rotation where the first gear wheel passes the untoothed recess, thereafter the first gear wheel engages one of the racks so the set unit can be injected, or the rotation can be continued to make the first gear wheel pass the next recess during which passing the set dose is increased by one more unit and so on until a dose with the wanted number of units is set.

A disadvantage by this construction is that the teeth of the racks and gearwheels alternating have to be brought in and out of engagement with each other with the inherit danger of clashing. As only a few racks separated by intermediary untoothed recess can be placed along the inner surface of the plunger only few increments can be made during a 360° rotation.

It is an objective of the invention to provide an injection device, which combines the advantages of the devices according to the prior art without adopting their disadvantages and to provide a device wherein is established a direct gearing, i.e. a gearing by which more transformations of rotational movement to linear movement and linear movement to rotational movement are avoided, between the injection button and the piston rod.

This can be obtained by an injection device comprising a housing wherein a piston rod threaded with a first pitch is non rotatable but longitudinally displaceable guided, a nut engaging the thread of the piston rod which nut can be screwed along the threaded piston rod away from a defined position in the housing to set a dose and can be pressed back to said defined position carrying the piston rod with it when the set dose is injected, a dose setting drum which can be screwed outward in the housing along a thread with a second pitch to lift an injection button with it up from the proximal end of the housing, which injection device is according to the invention characterised in that a gearbox is provided which provides a gearing between the axial movements of the injection button and the nut relative to the housing which gearing has a gearing ratio corresponding to the ratio of said second and first pitch.

In a preferred embodiment the gearing between the movements of the injection button and the nut is obtained by the gearbox comprising at least one gear wheel carried by a connector which projects from the gear box longitudinally displaceable but non rotatable relative to said gearbox and is integral with the nut, a first rack integral with a first element of the gearbox, which element is rotational but not longitudinally displaceable relative to the housing , and second element carrying a second rack projecting from said gearbox longitudinally displaceable but non rotatable relative to said first element and being coupled to the injection button to follow longitudinal movements of said button, the at least one gear wheel engaging the first and the second rack, respectively, and being dimensioned to provide a gearing by which a longitudinal movement of the second rack is transformed to a longitudinal movement of the connector with a gearing ratio for the mentioned longitudinal movements of the second rack and the connector relative to the housing, which gearing ratio corresponds to the ratio of said second to said first pitch.

In such a device only the forces necessary to drive the dose setting drum are transformed by a thread with a high pitch whereas the forces necessary to move the piston by injection is transmitted to said piston through a conventional gear with constantly engaging gears and racks.

The piston rod is provided with a stop for the movement of the nut along the thread of said piston rod. This way a dose setting limiter is provided in the classic way, which involves no additional members to prevent setting of a dose exceeding the amount of liquid left in the ampoule.

Figure 2:
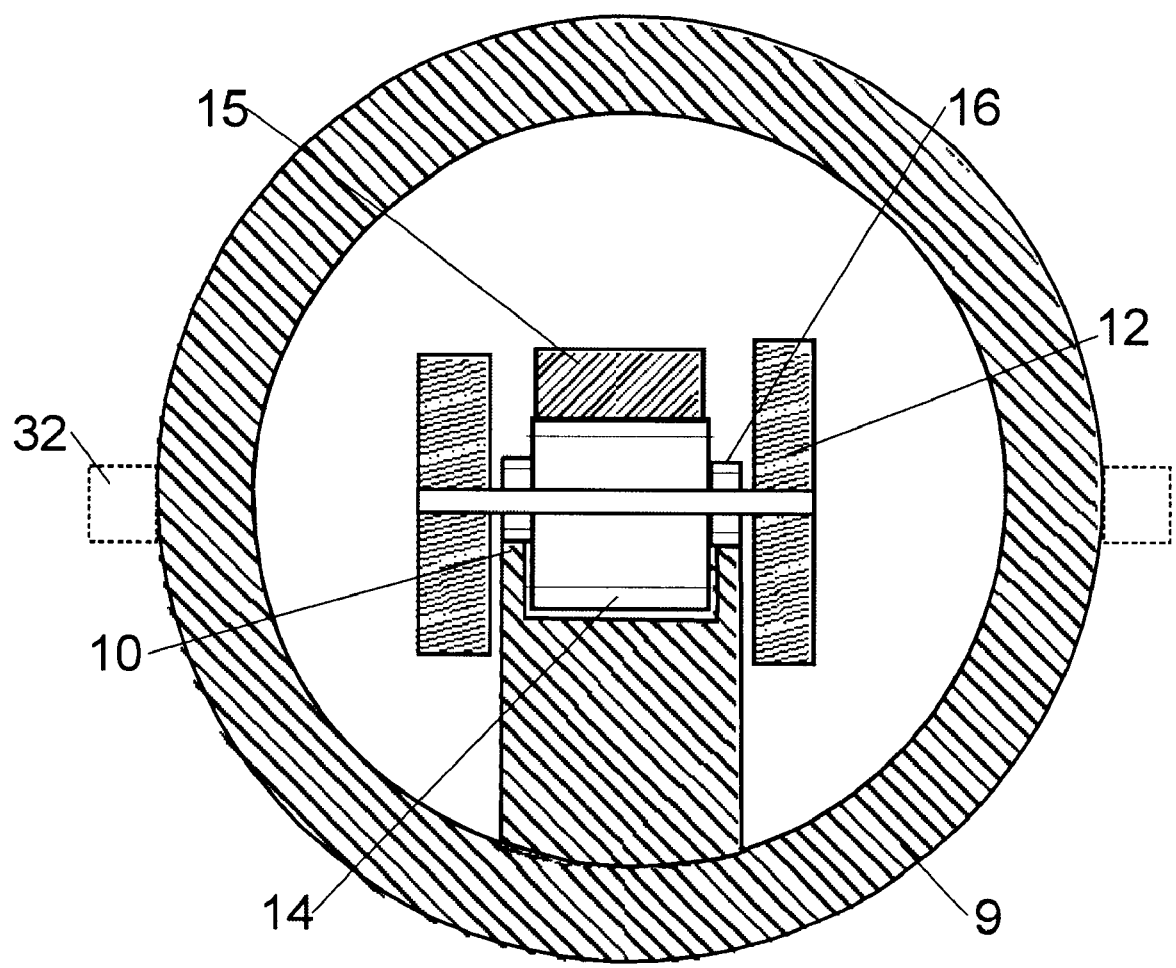
Figure 5:
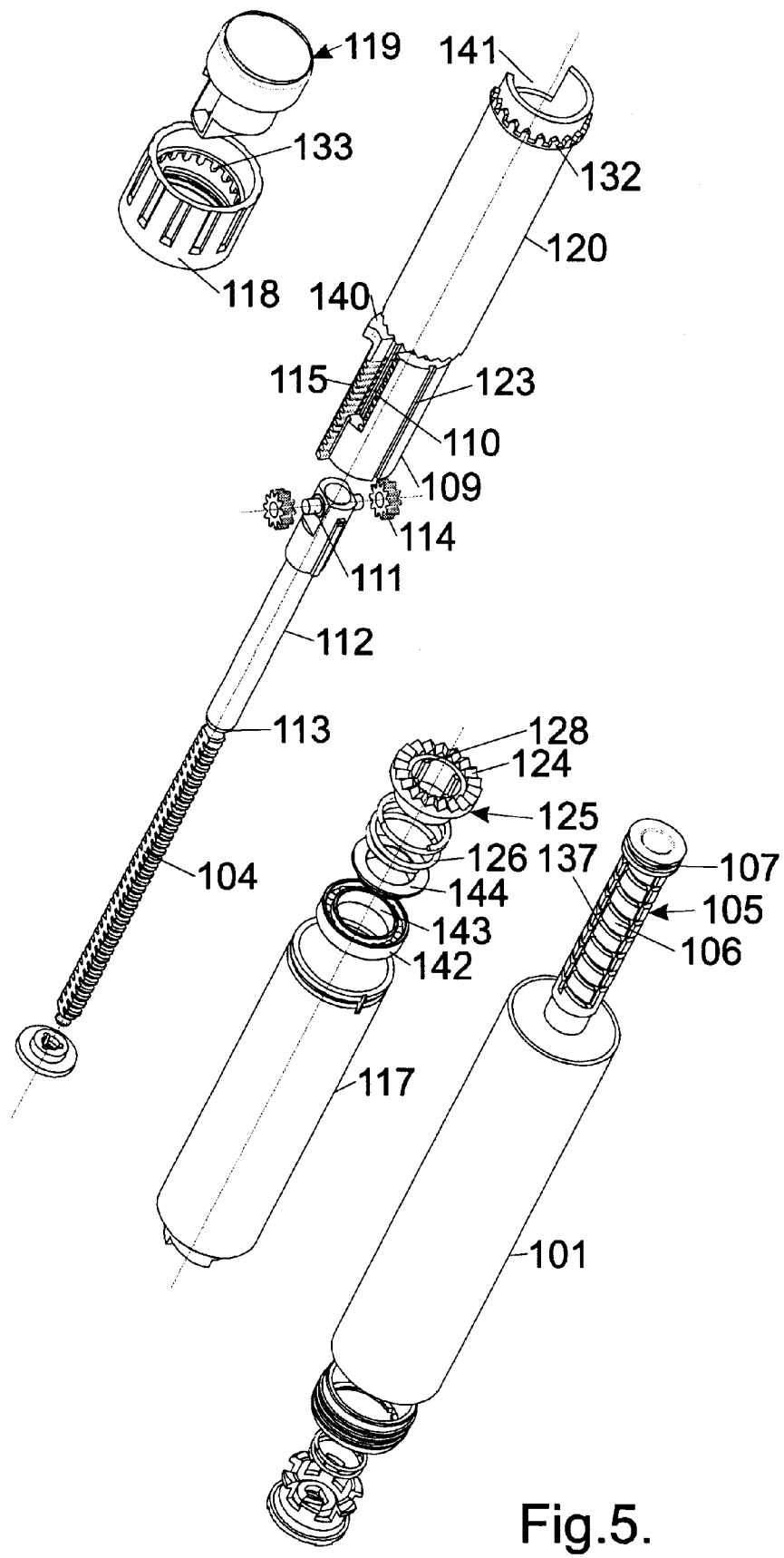

In the following the invention is described in further details with references to the drawing, wherein FIG. 1 schematically shows a sectional view of an injection device according to the invention, and FIG. 2 shows schematically a sectional view of the gear box along the line I—I in FIG. 1, FIG. 3 shows a longitudinal sectional view in the dose setting part of another embodiment of an injection device according to the invention, FIG. 4 shows a longitudinal sectional view perpendicular to the view in FIG. 3, and FIG. 5 shows an exploded picture of the of the device shown in FIGS. 3 and 4.

In the device shown in FIG. 1 an elongated cylindrical housing 1 has a partitioning wall 2 which divides the housing in a compartment containing a dose setting mechanism and a compartment 3 designed for the accommodation of a not shown ampoule. A threaded piston rod 4 has a not round cross section by which it fits through a central opening in the wall 2 so that the piston rod 4 can be displaced longitudinally through the central opening in the wall 2 but not rotated relative to this wall.

Concentrically with the housing 1 the wall 2 carries on its side turning away from the compartment 3 a tubular element 5 which is at a part of it adjacent to the wall 2 provided with an outer thread 6 and which has at its free end a circumferential recess 7. A ring shaped coupling element 8 on a gear box 9 engages the recess 7. By this coupling the gearbox is fixed in the housing 1 in a way that allows the gearbox 9 to rotate in the housing but not to be axially displaced relative to said housing.

In the gearbox 9 a gear wheel assembly comprising two integral gear wheels is journaled on a shaft 11, which runs perpendicular to the longitudinal axis of the device between two axial connection bars 12. The connection bars 12 project from the gear box towards the partition wall 2 and are connected to a nut 13 which adjacent to the wall 2 engages the thread of the piston rod 4. The gear wheel assembly comprises a gear wheel 14 with a large diameter engaging the teeth of a rack 15 which is guided in the gear box to be displaced in the longitudinal direction of the device, and a gear wheel 16 with a small diameter engaging a rack 10 in FIG. 2 extending in the longitudinal direction of the device on the inner wall of the gearbox 9. The gear wheel 16 with the small diameter may be divided into two gear wheels placed on each side of the of the gear wheel 14, and the rack on the inner wall of the gearbox 9 may have a longitudinal recess without any teeth to make room for the gear wheel 14.

A tubular dose setting drum 17 fitting into the housing 2 is at an end provided with an internal thread mating and engaging the outer thread 6 of the tubular element 5 and has at its other end a part with enlarged diameter forming a dose setting button 18. Due to the engagement with the thread 6 the dose setting drum 17 may be screwed in and out of the housing to show a number on a not shown helical scale on its outer surface in a not shown window in the housing 1.

A bottom 19 in a deep cup shaped element, which has a tubular part 20 fitting into the dose setting drum 17 and encompassing the gearbox 9, forms an injection button. Coupling means between the dose setting drum 17 and the cup shaped element ensures that rotation of the dose setting drum 17 is transmitted to the cup shaped element. Further the inner wall of the tubular part 20 has longitudinal recesses 22 engaged by protrusions 23 on the gearbox 9 so that rotation of the dose setting drum 17 via the cup shaped element is transmitted to the gearbox 9.

At the edge of the open end of the cup shaped element a rosette of V-shaped teeth are provided, which teeth engage a corresponding rosette of V-shaped teeth 24 on a ring 25 which is pressed against the edge of the cup shaped element by a spring 26 which is compressed between a not toothed side of the ring 25 and a round going shoulder 27 on the inner wall of the dose setting drum 17 at an inner end of the inner thread of this drum. The ring is provided with an inner recess, which is engaged by a longitudinal rib 28 on the tubular element 5 so that the ring 25 can be displaced in the axial direction of the device but cannot be rotated relative to the housing 1. Thereby a click coupling is established which makes a click noise when the V-shaped teeth at the edge of the cup shaped element by rotation of this element rides over the V-shaped teeth of the ring 25.

A head 29 on the projecting end of the rack 15 is with a play fixed at the bottom of the cup shaped element between the bottom 19 forming the injection button and an inner wall 30 near this bottom. The rack is fixed in a position with its head pressed against the wall 30 by a spring 31 between the bottom 19 and the head 29.

To set a dose the dose setting button 18 is rotated to screw the dose-setting drum 17 up along the thread 6. Due to the coupling 21 the cup shaped element will follow the rotation of the dose-setting drum 17 and will be lifted with this drum up from the end of the housing 1. By the rotation of the cup shaped element the V-shaped teeth 24 at the edge of its open end will ride over the V-shaped teeth of the non rotatable ring 25 to make a click sound for each unit the dose is changed. A too high set dose can be reduced by rotating the dose setting button 18 in the opposite direction of the direction for increasing the dose. When the dose setting drum is screwed up along the thread 6 on the tubular element 5 the ring 25 will follow the dose setting drum in its axial movement as the spring 26 is supported on the shoulder 27. The spring will keep the V-shaped teeth of the ring 25 and the cup shaped element in engagement and maintain in engagement the coupling 21, which may comprise Δ-shaped protrusions 32 on the cup shaped element engaging Λ-shaped recesses in an inner ring 33 in the dose setting button 18.

The rotation of the dose setting button 18 and the cup shaped element is further transmitted to the gearbox 9 through the protrusions 23 on this gearbox engaging the longitudinal recesses 22 in the inner wall of the tubular part 20 of said cup shaped element. The rotation of the gearbox 25 is through the connection bars 12 transmitted to the nut 13, which is this way screwed up along the thread of the piston rod 4 and lifted away from its abutment with the wall 2 when a dose it set. As the dose is set by moving the nut 13 on the very piston rod which operates the piston in the not shown ampoule in the compartment 3 a dose setting limiter, which ensures that the size of the set dose does not exceed the amount of medicament left in the ampoule, can easily be established by providing the piston rod 4 with a stop 35 which limits the movement of the nut 13 up along the piston rod 4.

Due to the confinement of the head 29 in the space between the bottom 19 and the wall 30 of the cup shaped element, the rack 15 is drawn with the injection button outward. Also the axial movement of the nut 13 relative to the housing 1 will be transmitted to the gear wheel assembly through the connection bars 12 and this movement will through the gearbox induce an outward movement of the rack 15. This induced outward movement have to be the same as the outward movement induced by outward movement of the injection button. This is obtained by dimensioning the gear wheels of the gearbox 9 so that the gear ratio for the movements of the connection bars 12 and the rack 15 relative to the housing corresponds to the ratio of the pitches for the thread on the piston rod and for the thread 6 for the longitudinal movement of the dose setting drum 17.

To inject a set dose the injection button is pressed by pressing on the bottom 19. In the initial phase of the pressing the spring 31 is compressed where after the pressing force is directly transmitted to the head 29 of the rack 15 and this way to the rack 15 itself. Through the gear box 9 the force is transformed and is transmitted through the connection bars 12 to the nut 13 which will press the piston rod 4 into the compartment 3 until the dose-setting drum 17 abuts the wall 2.

During the initial phase of the movement of the injection button the Δ-shaped protrusions 32 on the cup shaped element will be drawn out of their engagement with the Λ-shaped recesses in the ring 33. The dose-setting drum 17 can now rotate relative to the injection button and will do so when the Δ-shaped protrusions 32 press against a shoulder 34 at the bottom of the dose setting button 18. Only a force sufficient to make the dose setting drum rotate to screw itself downward along the thread 6 is necessary as the force necessary to make the injection is transmitted to the piston rod 4 through the gearbox 9. A helical reset spring 36 concentric with the dose setting drum can be mounted at the lower end of this drum and can have one end anchored in the dose setting drum 17 and the other end anchored in the wall 2. During setting of a dose this spring may be tighter coiled so that on the dose setting drum it exerts a torque approximately corresponding to the torque necessary to overcome the friction in the movement of the dose setting drum along the thread 6 so that the force which the user have to exert on the injection button is only the force necessary to drive the piston rod into an ampoule to inject the set dose.

It shall be noticed that use of only one size gear wheel which engages as well the rack 15, which is movable relative to the gear box 9, as the rack 10, which is unmovable relative to the gear box, provides a gearing ratio of 2:1 for the longitudinal movement relative to the syringe housing 1 for the movable rack 15 and the connector 12, which carries the shaft 11 of the gear wheel.

FIGS. 3 and 4 shows a preferred embodiment wherein only one size gear wheel is used and wherein elements corresponding to elements in FIGS. 1 and 2 are given the same references as these elements with a prefixed "1".

For manufacturing reasons minor changes are made. So the partitioning wall 102 and the tubular element 105 are made as two parts which are by the assembling of the device connected to each other to make the assembled parts act as one integral part. The same way the dose setting drum 117 and the dose setting button 118 are made as two parts, which are fixed firmly together.

A circumferential recess 107 is provided as an outer recess at the free end of the tubular part 105 and a ring shaped coupling element is provided as an inner bead 108 on the gearbox element 109 which bead engages the recess 107 to provide a rotatable but not axially displaceable connection between the tubular part 105 and the gearbox.

A tubular element 120 having ridges 122 which engages recesses 123 on the gearbox is at its upper end closed by a button 119 from which a force provided by pressing this button is transmitted to the tubular element 120.

The gearbox is formed by two shells, which together form a cylinder fitting into the tubular element where the shells are guided by the engagement between the ridges 122 and the recesses 123. Racks 110 and 115 are provided along edges of the shells facing each other. One shell forming the gearbox part 109 is provided with the inner bead 108, which engages the circumferential recess 107 at the end of the central tubular part 105 and carries the rack 110. The other shell is axially displaceable in the tubular element 120 and forms the rack 115. At its outer end projecting from the gearbox the shell carrying the rack 115 is provided with a flange 140 which is positioned in a cut out 141 in the end of the tubular element 120 carrying the button 119 so that this button and the tubular element 120 can be moved so far inward in the device that the engagement of the teeth 132 and 133 can be released before the button 119 abuts the flange 140.

A tubular connection element 112 connects the threaded piston rod 104 with the gearbox. At its end engaging the piston rod 104 the connection element has a nut 113 with an internal thread mating the external thread of the piston rod. At its end engaging the gear box the connection element is provided with two pins 111 projecting perpendicular to the longitudinal axis of the connection element 112 at each side of this element. Each pin 111 carries a gear wheel 114 which is placed between and engages the two racks 110 and 115. This way the connection element 112 will be rotated with the gear box but can be displaced axially relative to said gear box when the racks 110 and 115 are moved relative to each other. In practice it will be the rack 115, which is moved relative to the gearbox element 109 and the housing and will by the shown construction result in a movement of the connection element 112 relative to housing a distance which is half the distance which the rack 115 is moved. A ring 125 which is at its periphery provided with a rosette of teeth 124 and has a central bore fitting over the central tube in the housing 101 so that this ring 125 can be axially displaced along said central tube 105, but internal ridges 128 in the central bore of the ring 125 engages longitudinal recesses 137 in the central tube to make the ring non rotatable in the housing so that a rosette of teeth at the edge of the tubular element 120 can click over the teeth 124 of the ring when said tubular element is rotated together with the dose setting drum 117. A spring 126 working between the ring 125 and an internal shoulder 127 provided in the dose setting drum 117 makes the ring follow the tubular element 120 when this element with the dose setting drum is moved longitudinally in the housing. To make the dose setting drum easy rotatable, especially when said dose setting drum is pressed inward in the housing, a roller bearing having an outer ring 142 supported by the shoulder 127 and an inner ring 143 supporting a pressure bushing 144 which supports the spring 126. By the provision of this smooth running support only very small axial forces are needed to rotate the dose setting drum 117 back to its zero position when a set dose is injected. This solution replaces the provision of a reset spring as the spring 36 in FIG. 1. The bearing is shown as a radial bearing but can be replaced by an axial bearing.

What is claimed is:

1. An injection device comprising:
   a. a housing having a proximal end and a distal end;
   b. a threaded piston rod having a first pitch, the piston rod being linearly displaceable in the housing but being rotatably fixed with respect to the housing;
   c. a displaceable nut that moves relative to the housing, the nut engaging the thread of the piston rod so that the nut can screw along the thread of the piston rod, thereby being capable of moving along the piston rod in proximal direction from a first position on the piston rod to a second position on the piston rod, the displacement of the nut along the piston rod in a proximal direction defining a quantity of medication to be injected by the injection device,
   d. a dose setting drum having an injection button disposed on an end thereof, the drum having a threaded surface with a second pitch, the dose setting drum engaging the housing and rotatable within the housing so that it may be screwed outward from the proximal end of the housing;
   e. a gear box assembly coupling axial movement of the injection button with axial movement of the nut, the gear box providing a gearing having a ratio corresponding to the ratio of the second pitch to the first pitch.

2. The injection device of claim 1, wherein the gear box assembly that couples axial movement of the injection button with the nut comprises:
   a. at least one gear wheel carried by a connector that projects from the gear box assembly, the connector being longitudinally displaceable but non-rotatable with respect to the gearbox and being integral with the nut;
   b. a first rack that is integral with a first element of the gearbox, the first element being rotatable but not longitudinally displaceable relative to the housing;
   c. a second gear box element carrying a second rack projecting from the gearbox, the second rack being longitudinally displaceable but non-rotatable with respect to the first element and being coupled to the injection button to follow longitudinal movement of the button; and
   d. wherein the at least one gear wheel engages the first and second racksand is dimensioned to provide a gearing by which longitudinal movement of the second rack is transformed into longitudinal movement of the connector with a gearing ratio for the longitudinal movements of the second rack and connector relative to the housing being in the ratio of the second pitch to the first pitch.

3. The injection device of claim 2, wherein the gearing ratio is 2:1.

4. The injection device of claim 2, wherein the piston rod has a stop.

5. An injection device comprising:
   a. a housing having a proximal end and a distal end;
   b. a linearly displaceable dose setting member protruding from the proximal end of the housing, the dose setting member having a proximal end adapted for receiving an axial force from a finger of a person administering an injection with the device, the dose setting member also having a threaded surface with a pitch P1, the dose setting member being linearly displaceable as a result of rotation of the member relative to the housing;
   c. a non-rotating threaded piston rod, the piston rod residing, at least partially, within the housing and a portion of the piston rod extending distally from the distal end of the housing, the piston rod being threaded and having a pitch P2;
   d. a threaded nut that screws along the piston rod, the nut being linearly displaceable in a proximal direction from a first position where it abuts a stop in the distal end of the housing, the nut being rotationally coupled to the dose setting member so that rotation of the dose setting member causes the nut to screw along the piston rod;
   e. a gearbox coupling axial movement of the dose setting member in a proximal direction with axial movement of the nut in a proximal direction, the gearbox having a gearing such that the ratio of movement of the dose setting element to movement of the nut is the same as the ratio of P2 to P1; and
   f. a means for preventing rotation of the nut relative to the piston rod when a force is exerted on the proximal end of the dose setting member.

6. The device of claim 5, wherein the ratio of P2 to P1 is approximately 2:1.

7. The device of claim 5, wherein the gearing ratio is at least 2:1.

8. The device of claim 7, wherein the piston rod has a stop.

9. The device of claim 7, wherein gear box assembly comprises: a housing, a first rack coupled to the injection button and a second rack that is integral with the gearbox housing, a gear wheel that can roll along the racks, a gear wheel carrying element that is coupled to the gear wheel at one end and the nut at another end, and wherein the first and second racks are coupled by the gear wheel.

10. The injection device of claim 9, wherein the gearbox assembly is axially fixed with respect to the housing.

11. An injection device comprising:
   a. a housing for a dose setting and injecting mechanism, the housing having a proximal end and a distal end;
   b. a rotatable linearly displaceable dose setting member having a proximal end on which an injection button is mounted;
   c. a threaded piston rod, the piston rod being rotationally fixed but axially displaceable;
   d. a nut that screws along the piston rod in a proximal direction from a first position, the nut being rotatably coupled to the dose setting member so that rotation of the nut corresponds to axial displacement of the dose setting member;
   e. a linear force coupling means for coupling linear force exerted on the injection button, wherein the force exerted on the nut is greater than the force exerted on the injection button; and f. a means for preventing rotation of the nut when linear force is exerted on the injection button.

12. The device of claim 11, wherein the linear force coupling means comprises a gearing that couples axial movement of the injection button to the nut without causing rotation of the nut.

13. The device of claim 11, wherein the coupling means comprises a first rack that is coupled to the injection button and a second rack and a gear assembly coupling the first rack to the second rack.

14. The injection of claim 11, wherein the gearbox is free to rotate within the housing.

15. An injection device comprising:
 a. a housing having a proximal end;
 b. a non-rotatable threaded piston rod;
 c. a nut that screws along the piston rod in a proximal direction from a defined position;
 d. a dose setting member protruding from the proximal end of the housing and having injection button located on a proximal end thereof, the injection button adapted to receive a linear force;
 e. a gear box assembly disposed within the housing, the gear box assembly coupling axial motion of the injection button with axial motion of the nut without causing rotation of the nut, thereby driving the piston rod in a distal direction when the injection button is moved distally; and
 f. wherein the gear box assembly causes the force exerted on the piston rod nut to be greater than the force exerted on the injection button.

16. The injection device of claim 15, wherein the force exerted on the piston rod is approximately at least twice that of the force exerted on the injection button.

* * * * *